(12) United States Patent
Biesel et al.

(10) Patent No.: US 8,038,643 B2
(45) Date of Patent: Oct. 18, 2011

(54) DEVICE AND METHOD FOR LOADING A PATIENT CONNECTOR FOR PERITONEAL DIALYSIS WITH A CLOSURE PLUG

(75) Inventors: Wolfgang Biesel, Ottweller (DE); Reinhold Reiter, Crema (IT); Alain Veneroni, Spino d'Adda (IT)

(73) Assignee: Fresenius Medical Care Deutschland GmbH, Bad Homburg (DE)

( * ) Notice: Subject to any disclaimer, the term of this patent is extended or adjusted under 35 U.S.C. 154(b) by 498 days.

(21) Appl. No.: 10/587,924

(22) PCT Filed: Jan. 27, 2005

(86) PCT No.: PCT/DE2005/000126
§ 371 (c)(1),
(2), (4) Date: Aug. 2, 2006

(87) PCT Pub. No.: WO2005/075008
PCT Pub. Date: Aug. 18, 2005

(65) Prior Publication Data
US 2008/0275382 A1 Nov. 6, 2008

(30) Foreign Application Priority Data
Feb. 3, 2004 (DE) .......................... 10 2004 005 372

(51) Int. Cl.
*A61M 1/00* (2006.01)
*A61M 25/18* (2006.01)
*A61M 39/00* (2006.01)
*A61M 39/10* (2006.01)

(52) U.S. Cl. ......................................... 604/29; 604/533

(58) Field of Classification Search ................... 604/29, 604/246, 249, 256, 533
See application file for complete search history.

(56) References Cited

U.S. PATENT DOCUMENTS
3,707,972 A * 1/1973 Villari et al. ................. 604/249
4,306,705 A * 12/1981 Svensson .................. 251/149.9
4,745,950 A 5/1988 Mathieu
(Continued)

FOREIGN PATENT DOCUMENTS
DE 94 19 630.3 U1 3/1995
(Continued)

OTHER PUBLICATIONS
International Search Report.

*Primary Examiner* — Kevin C Sirmons
*Assistant Examiner* — Andrew Gilbert
(74) *Attorney, Agent, or Firm* — Collard & Roe, P.C.

(57) ABSTRACT

The invention relates to a device for loading a patient connector for peritoneal dialysis with a closure plug. To permit an arbitrary number of disconnection/connection procedures with patient connectors that insert a sterile closure plug into the patient's abdominal connector during disconnection, a device for loading a patient connector for peritoneal dialysis with a closure plug is suggested, said device consisting of a housing containing a closure plug and of means for transferring the closure plug out of the device and into a patient connector. This permits loading, under sterile conditions, of a patient connector whose closure plug has already been used with a new closure plug. By loading a new closure plug, the push-button with which the closure plug is inserted is returned to its starting position, so that the patient connector is again available for a connection/disconnection procedure.

12 Claims, 9 Drawing Sheets

U.S. PATENT DOCUMENTS

| | | |
|---|---|---|
| 5,228,646 A | 7/1993 | Raines et al. |
| 5,694,978 A | 12/1997 | Heilmann et al. |
| 5,713,850 A | 2/1998 | Heilmann et al. |
| 7,137,974 B2 * | 11/2006 | Almasian et al. ............. 604/411 |
| 2001/0041873 A1 * | 11/2001 | Dopper et al. ................ 604/249 |
| 2003/0216712 A1 | 11/2003 | Kessler et al. |

FOREIGN PATENT DOCUMENTS

| | | |
|---|---|---|
| DE | 198 14 047 C1 | 5/1999 |
| DE | 100 55 283 B4 | 6/2002 |
| EP | 0 198 14 407 A | 10/1986 |
| EP | 0 715 860 B1 | 6/1996 |
| WO | WO 2004/011077 A | 2/2004 |

* cited by examiner

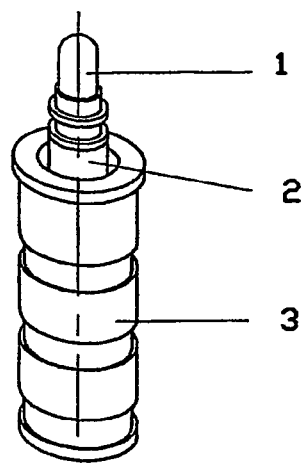
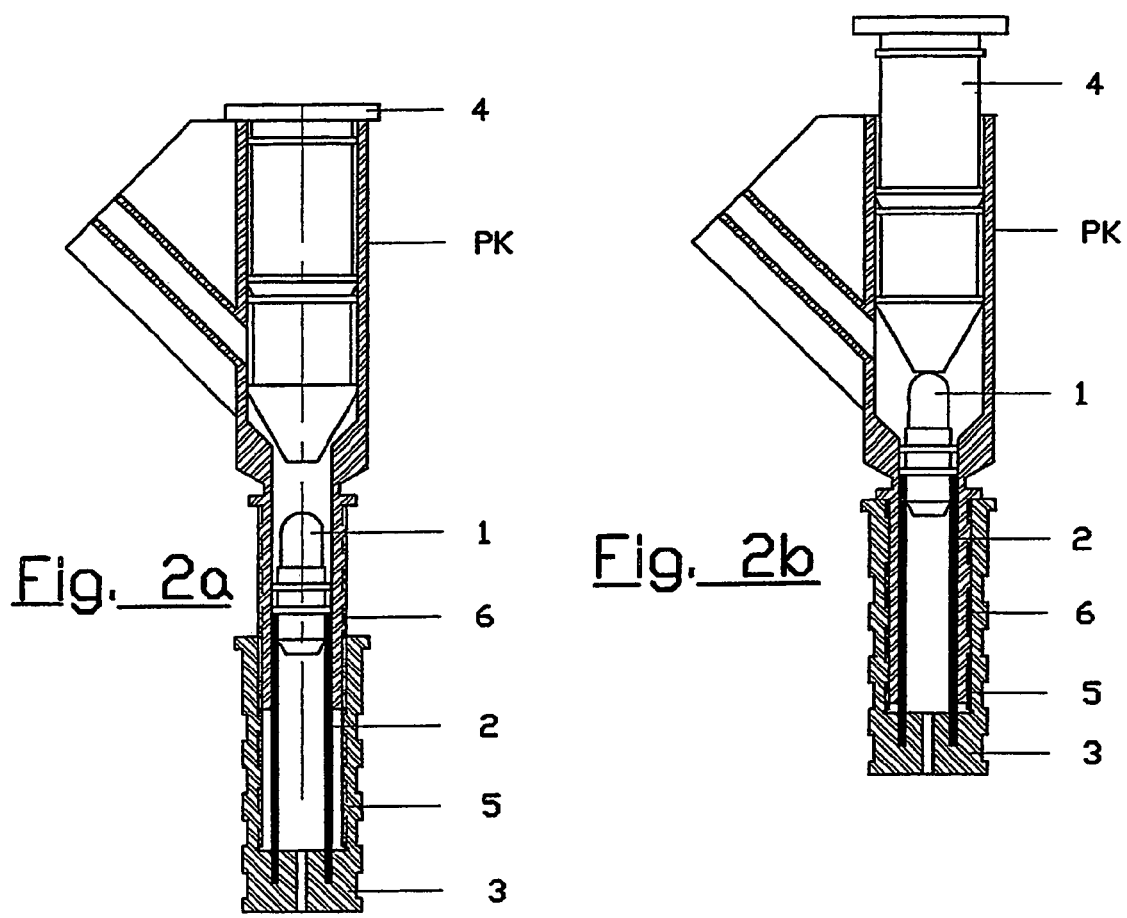

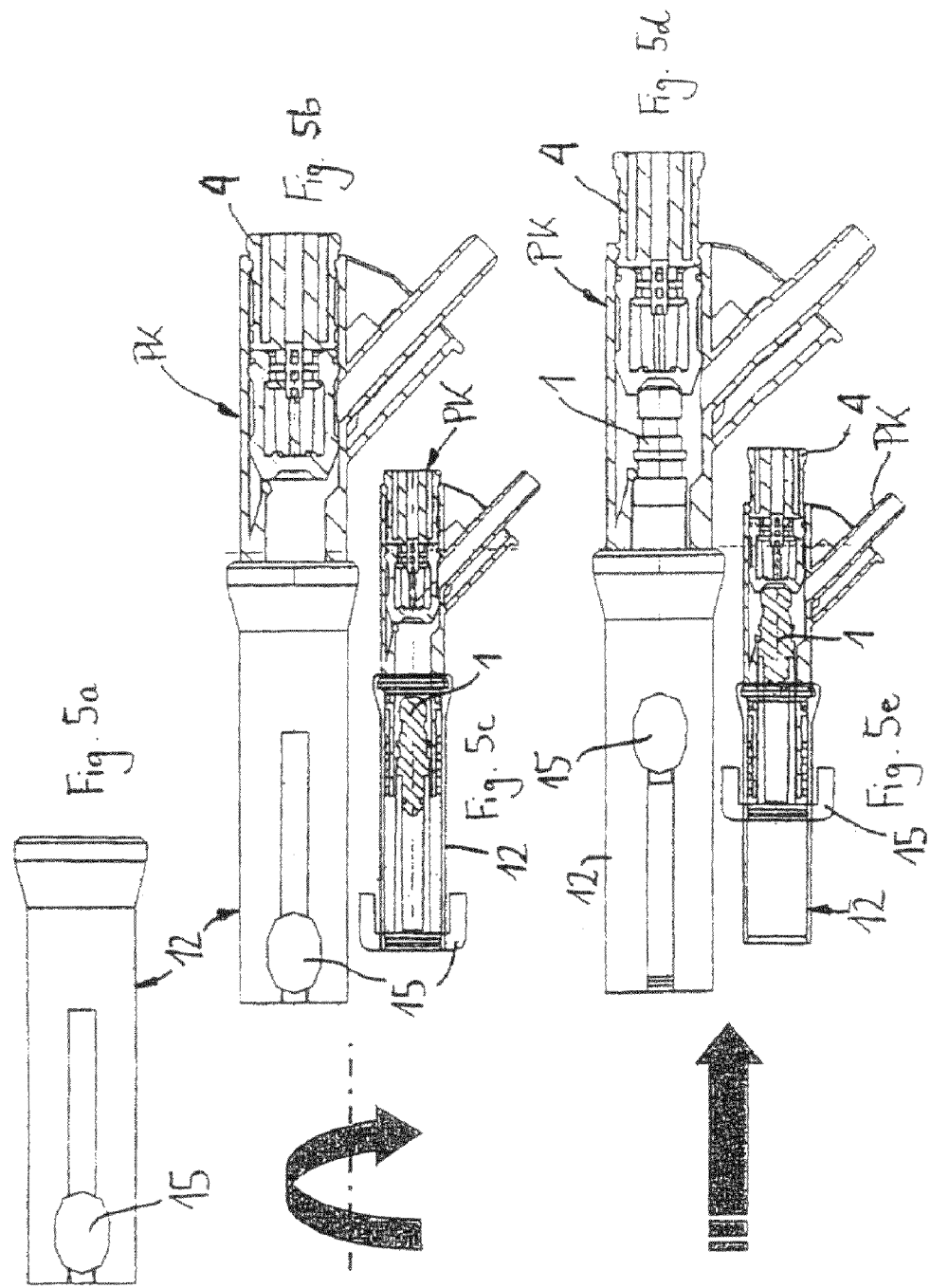

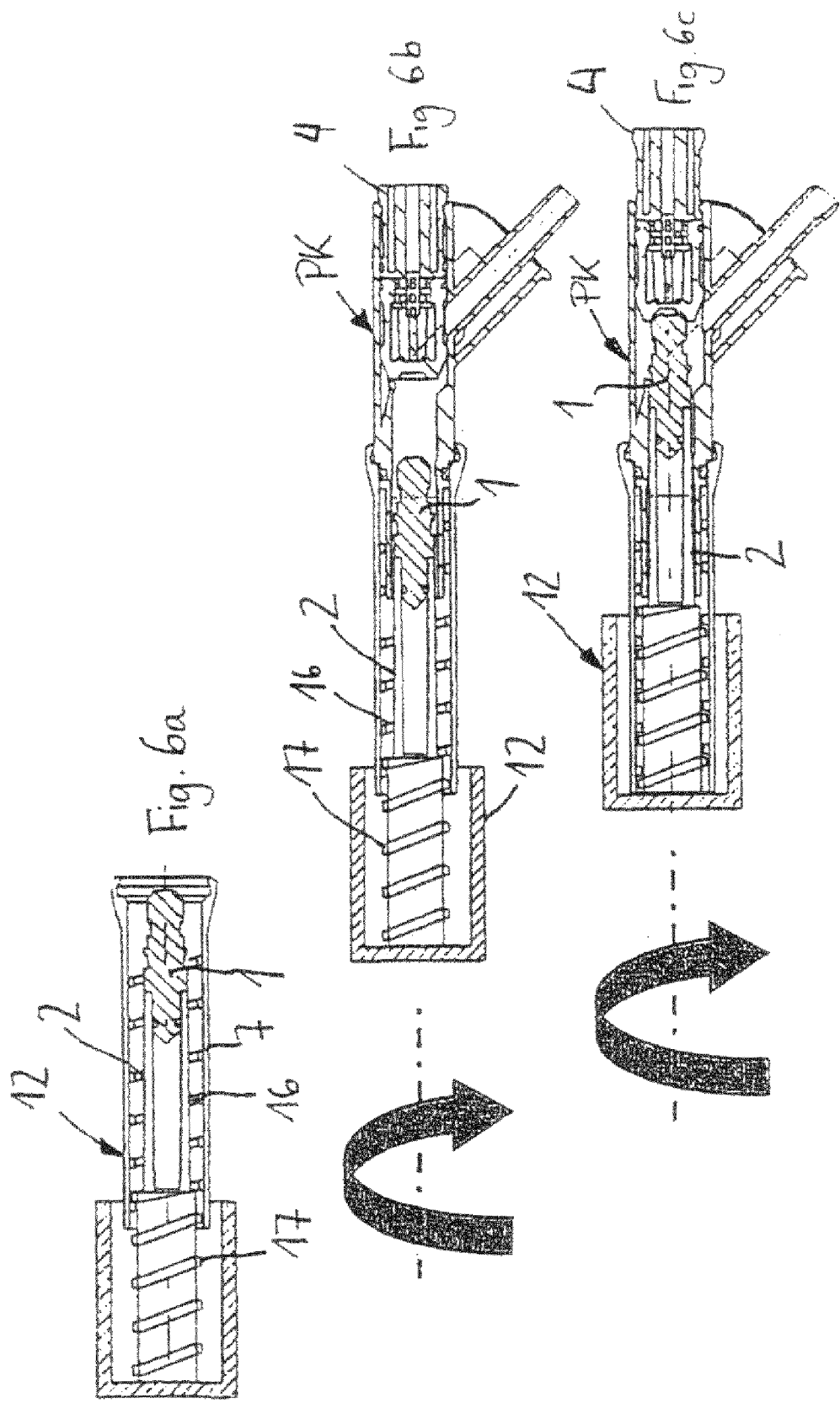

DEVICE AND METHOD FOR LOADING A PATIENT CONNECTOR FOR PERITONEAL DIALYSIS WITH A CLOSURE PLUG

CROSS REFERENCE TO RELATED APPLICATIONS

Applicants claim priority under 35 U.S.C. §119 of German Application No. 10 2004 005 372.3 filed Feb. 3, 2004. Applicants also claims priority under 35 U.S.C. §365 of PCT/DE2005/000126 filed Jan. 27, 2005. The international application under PCT article 21(2) was not published in English.

The invention relates to a device and a method for loading a patient connector for peritoneal dialysis with a closure plug.

Patient connectors for peritoneal dialysis are known, for example, from EP 0 715 860 B1 or U.S. Pat. No. 6,482,189. These connectors permit sterile connection and disconnection of patients undergoing peritoneal dialysis treatment. With patient connectors of this kind, a closure plug is inserted on completion of peritoneal dialysis into the connector of the tube portion going into the patient's abdominal cavity. The entrance to the patient's abdominal cavity is thus closed off in sterile manner.

If the patient wishes to be disconnected from his/her tubing set, and later reconnected again, this is in principle possible provided the closure plug has not already been used. To be disconnected and reconnected again twice or more is thus not possible. The solution to this problem has hitherto consisted in providing two patient connectors, each with a closure plug, one behind the other in the tubing set with a short length of tubing between them. This arrangement allows the patient to be disconnected and reconnected again once during the treatment. The patient connector used for the first disconnection procedure is simply disposed of before the patient is reconnected. However, the additional patient connector including the short piece of tubing is relatively expensive, especially in view of the fact that the second patient connector is only needed in 10% of cases. Moreover, only one such disconnection/reconnection procedure is possible with one and the same set of tubing.

The object of this invention is thus to make any desirable number of disconnection/reconnection procedures possible with patient connectors that insert a sterile closure plug into the patient's abdominal connector during the disconnection procedure, and to minimize the associated costs.

This object is established by a device for loading a patient connector for peritoneal dialysis with a closure plug, said device consisting of a housing containing a closure plug and of means for transferring the closure plug out of the device and into a patient connector.

A device of this kind permits loading, under sterile conditions, of a patient connector whose closure plug has already been used with a new closure plug. By loading the patient connector with a new closure plug of the kind known from U.S. Pat. No. 6,482,189, the push-button with which the closure plug is inserted is also returned to its starting position, so that the patient connector is available for another connection/disconnection procedure. A patient connector can be reloaded several times in this way, the advantage being that costs are only incurred when a connection/disconnection procedure is actually intended.

A development of the invention consists in that the housing is connectable with the portion of the patient connector into which the closure plug is to be transferred.

Connecting the housing with the patient connector permits easy transfer of the closure plug under sterile conditions. Operating errors can practically be ruled out, so that no loss of sterility of the closure plug need be feared, nor loss thereof during transfer.

According to the invention, the housing can be connected with the patient connector by means of a positive connection, especially a screwed, pin-type or keyed joint.

It is also possible for the housing to be connected with the patient connector by means of a friction-type connection, especially a press-fit or a clamping joint.

It is also to advantage that the means for transferring the closure plug is engineered as a push-button or turning knob at the opposite end of the housing to where the closure plug exits the same, with an intermediate element being provided if necessary between the push-button or turning knob and the closure plug.

When the push-button or turning knob is actuated, the closure plug is moved linearly within the housing until it is finally pushed out of the housing and into the patient-connector opening provided therefor. If necessary, an intermediate element can be provided between the push-button or turning knob and the closure plug.

The invention provides for the closure-plug transfer means to be designed as a holder for the closure plug, the retention force exerted by the holder on the closure plug being lower than the retention force exerted on the closure plug in the patient connector.

Accommodated in a holder of this kind, the closure plug is inserted into the opening of the patient connector, and because of the greater retention force in the latter, detaches from the housing and is held ready for use in the patient connector.

It is additionally expedient that prior to transfer, the closure plug is held in a retracted position within the housing so as to be protected from contamination.

On account of the retracted position of the closure plug, it is prevented from being touched and hence contaminated by the user.

The scope of the invention also includes a method for loading a patient connector for peritoneal dialysis with a closure plug, said method involving connection of a housing containing a closure plug with the portion of a patient connector into which the closure plug is to be transferred, and subsequently transferring the closure plug from the housing into the patient connector.

It is expedient here that the housing is connected with the patient connector by means of a positive connection or a friction-type connection.

It is furthermore to advantage that the closure plug is transferred from the housing into the patient connector by way of linear motion.

The invention also provides for the linear displacement of the closure plug to be triggered by actuation of a push-button or turning knob.

Finally, it is also within the scope of the invention that the closure plug is transferred on account of the retention force exerted by the holder on the closure plug in the housing being lower than the retention force exerted on the closure plug in the patient connector.

Embodiments of the invention will now be explained by reference to the drawings.

FIG. 1 is a perspective view of a device according to the invention;

FIG. 2a and FIG. 2b are sectional views illustrating the reloading of a patient connector with the help of the device illustrated in FIG. 1;

FIG. 5a to FIG. 5e illustrate in sectional and partially sectional views the reloading process with a device for moving the closure plug;

FIG. 6a to FIG. 6c are sectional views illustrating the reloading process with a device for transferring the closure plug by means of screw motion.

Figure 3:
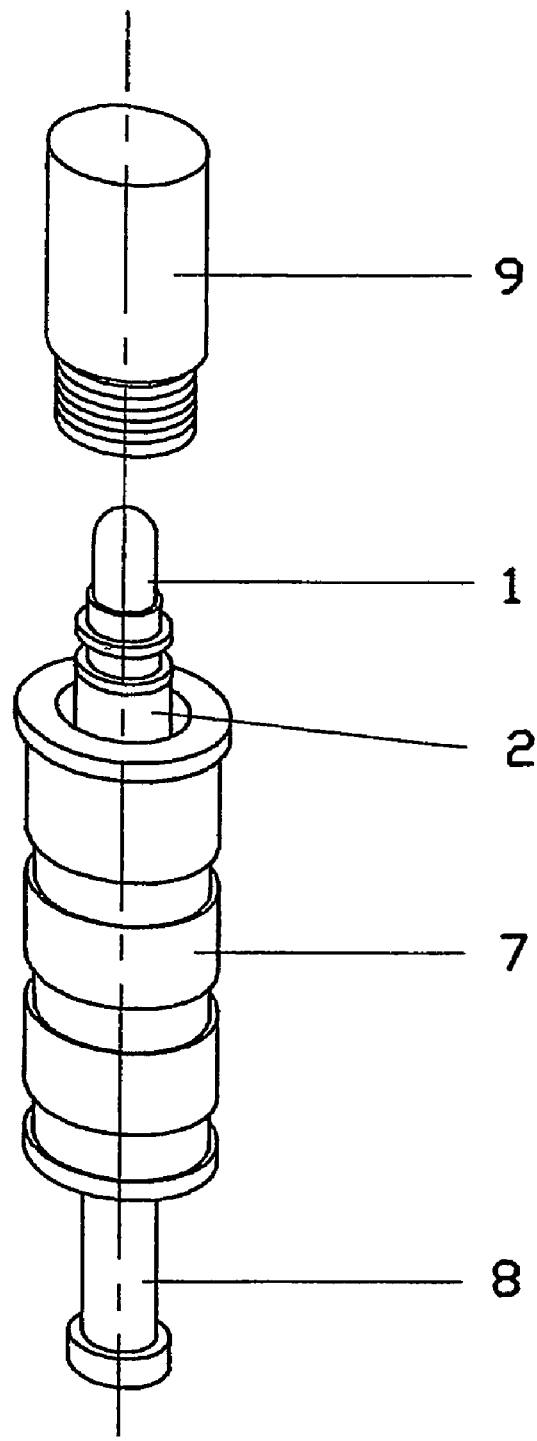
FIG. 3 is a perspective view of another version of the device.

As is illustrated in FIG. 1, a simple embodiment of the device according to the invention consists in that a sterile closure plug 1 is disposed on a cylindrical tube section 2 which is attached at its base to a protective cap 3. The protective cap 3 is for handling the device, so that neither the closure plug 1 nor the tube section 2 needs to be touched while the patient connector (PK) is being reloaded.

FIG. 2a illustrates the start of the reloading procedure for a patient connector (PK) of the type known from U.S. Pat. No. 6,482,189: the push-button 4 of the patient connector (PK) is still in the depressed position following the previous insertion of a closure plug. The tube section 2 with the new, sterile closure plug 1 is inserted into the patient connector (PK) at the socket-shaped end opposite the push-button 4, until the new closure plug 1 makes contact with the lower end of the push-button 4. Subsequently (FIG. 2b), the internal thread 5 of the protective cap 3 is screwed onto the external thread 6 of the patient connector (PK), causing the closure plug 1 to exert pressure on the push-button 4 of the patient connector (PK) and push it back up to its starting position. FIG. 2b shows the final position of the reloading procedure: the push-button 4 is once again in its starting position and can exert pressure on the closure plug 1 immediately in front of it in the socket of the patient connector (PK); as a result, a further connection/disconnection procedure can be carried out with the patient connector (PK). Due to the fact that the retention force between the patient connector (PK) and the closure plug 1 is greater than that between the tube section 2 and the closure plug 1, the closure plug 1 remains in the patient connector (PK) when the protective cap 3 and the tube section 2 attached thereto are removed from the patient connector (PK).

The closure plug, which is sterile at the start of the reloading procedure (the entire reloading unit advantageously comes as a sterile package), is not touched at all during the reloading procedure. This can be realised by having the closure plug 1 initially located in a retracted position within the housing 7, so that it is protected against touch-contamination.

FIG. 3 illustrates another embodiment of a device according to the invention. In this embodiment, the closure plug 1 is likewise disposed on a cylindrical tube section 2 within a cylindrical housing 7, the tube section 2 being linearly movable within the housing 7.

The closure plug 1 is transferred to a patient connector (PK) in a manner analogous to the procedure described above, except that the linear movement of the closure plug 1 is triggered by actuating the actuating button 8—possibly with interposition of an intermediate element between the actuating button 8 and the tube section 2.

So that it can be seen better prior to the reloading procedure, the closure plug 1 in FIG. 3 is shown pushed out of the housing 7 (although the actuating button 8 has not yet been actuated). Prior to its insertion into the patient connector (PK), the closure plug is kept sterile and protected from contamination within the housing 7. It can be additionally protected by the cap 9, which is also illustrated. For long-term storage, added protection can be provided by weld-packaging the sterile device.

The reloading process will now be explained as used with a so-called "organizer", that is, a device which holds the patient connector (PK) and considerably facilitates handling by the patient.

Figure 4A:
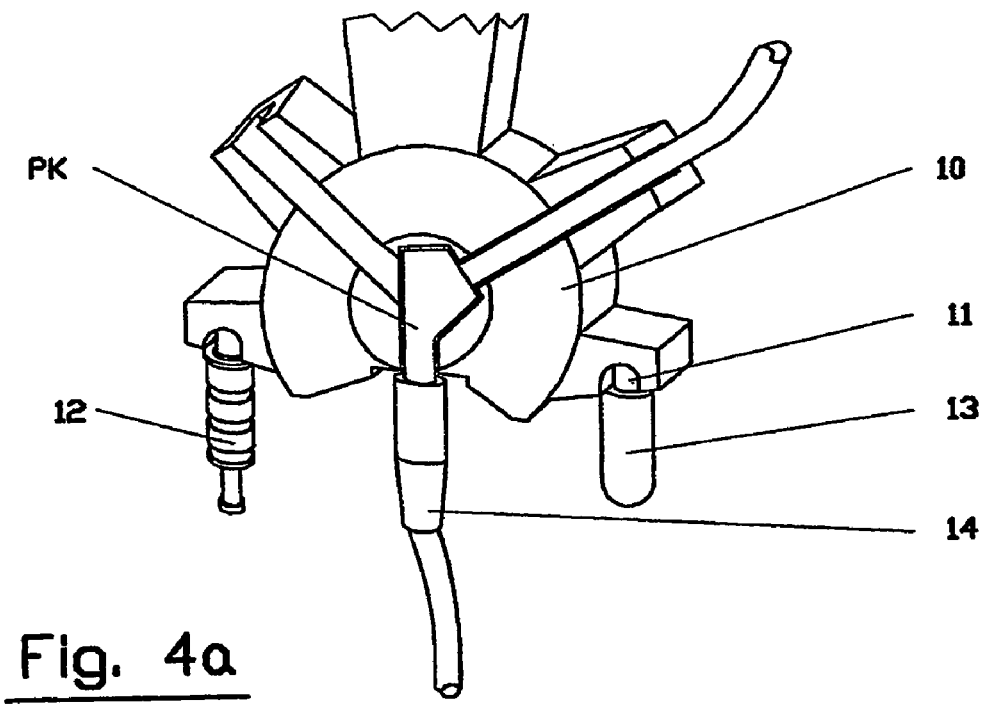
FIG. 4a to FIG. 4i illustrate the reloading of a patient connector using a so-called "organizer"

As illustrated in FIG. 4a, the patient connector (PK), in this case the one known from DE 198 14 047 C1, is inserted into the central area of the organizer 10. Also disposed on the organizer 10 are a disinfection cap 11 and the reloading device 12 known from FIG. 3.

Figure 4B:
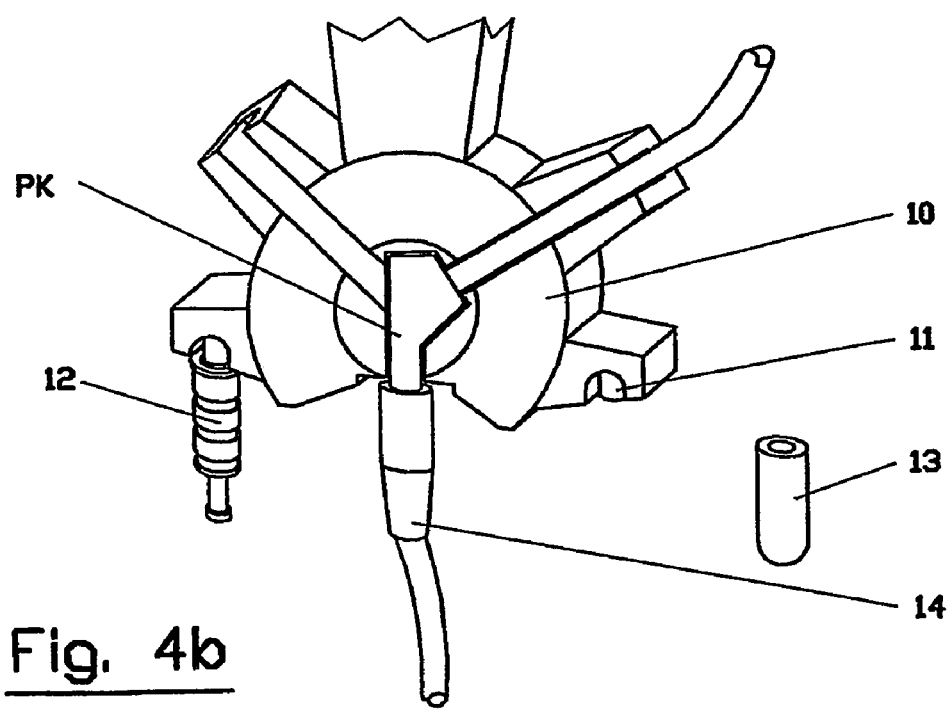

The organizer 10 is prepared further for the disconnection procedure by removing a protective cap 13 from the disinfection cap 11, as shown in FIG. 4b.

Figure 4C:
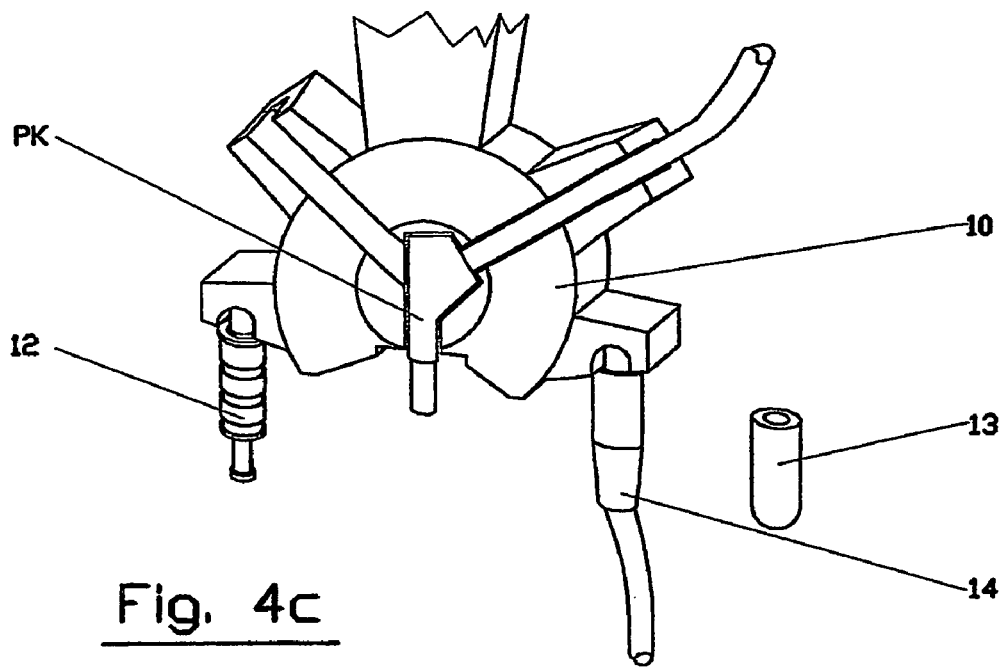

After completion of these preparations, the disconnection procedure can begin. To start with, as shown in FIG. 4c, the abdominal connector 14—which is closed with a closure plug 1—is disconnected from the patient connector PK and connected with the disinfection cap 11.

Figure 4D:
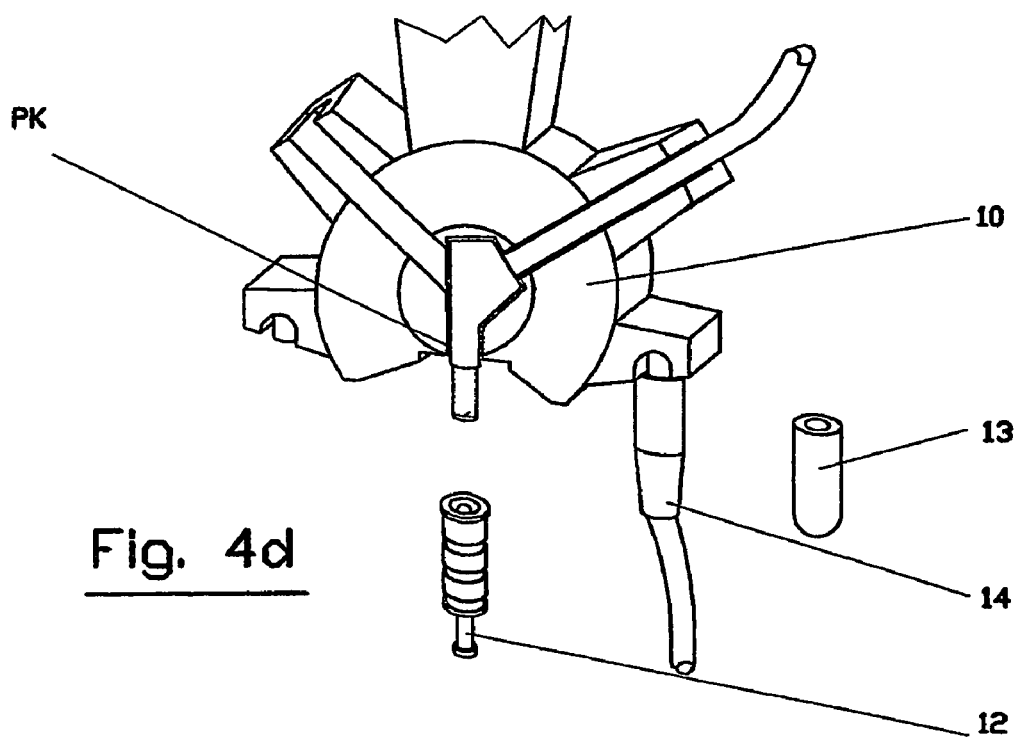

Then (FIG. 4d), the reloading device 12 is detached from the organizer 10. The reloading device 12 contains a new, sterile closure plug 1, which is protected there from contamination. The cap 9 remains on the organizer 10.

Figure 4E:
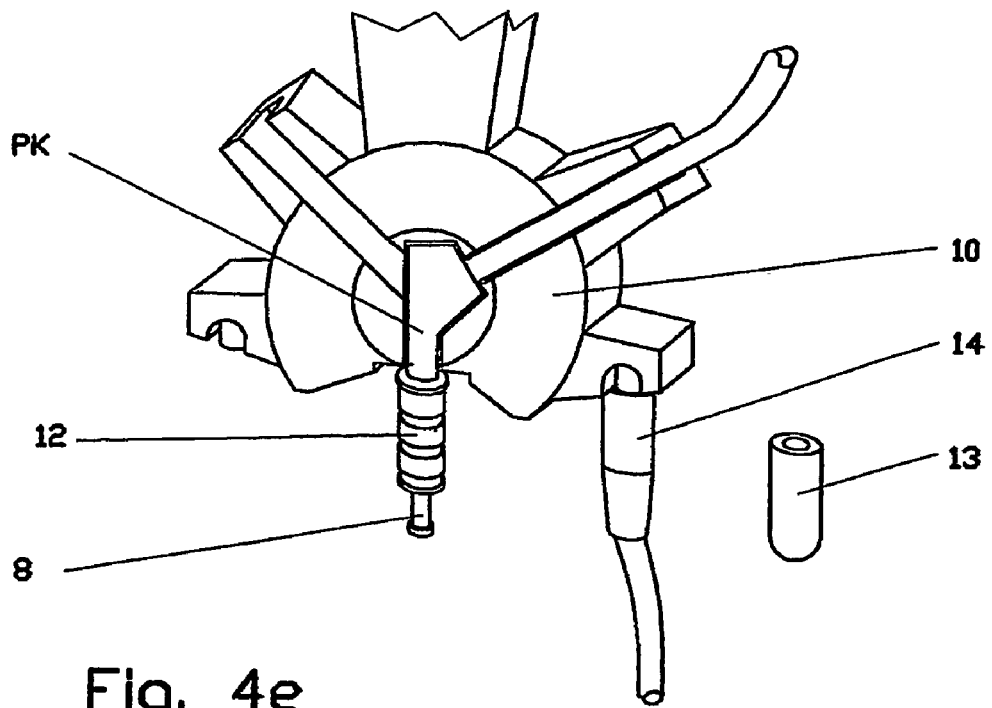
Figure 4F:
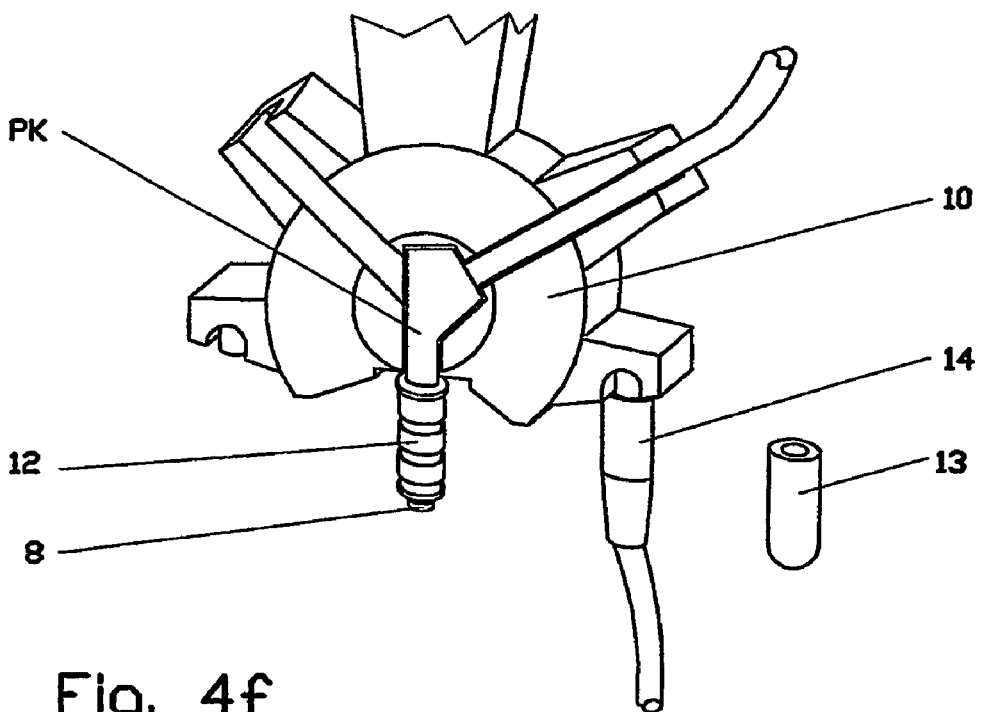
Figure 4G:
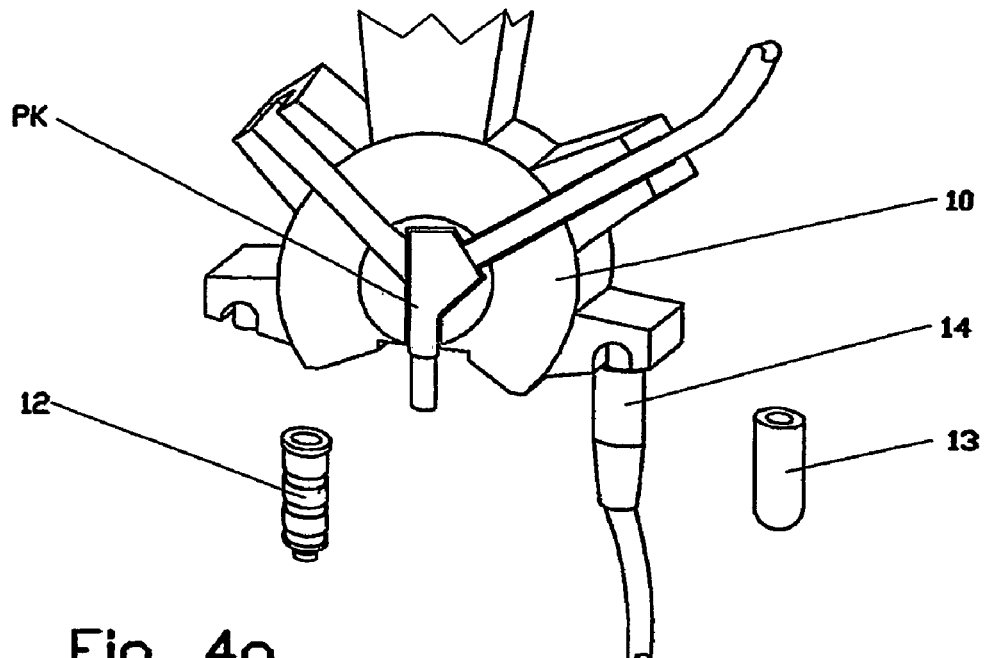

The reloading device 12 is then connected with the patient connector PK in the organizer 10 (FIG. 4e) and the actuating button 8 of the reloading device 12 pressed (FIG. 4f) in order to transfer the new closure plug 1 into the patient connector, and to move its push-button back into the starting position.

The patient connector is now ready for a new connection procedure.

To this end, the reloading device 12, from which the closure plug 1 has been removed, is first of all disconnected from the patient connector PK, as shown in FIG. 4 g.

Figure 4H:
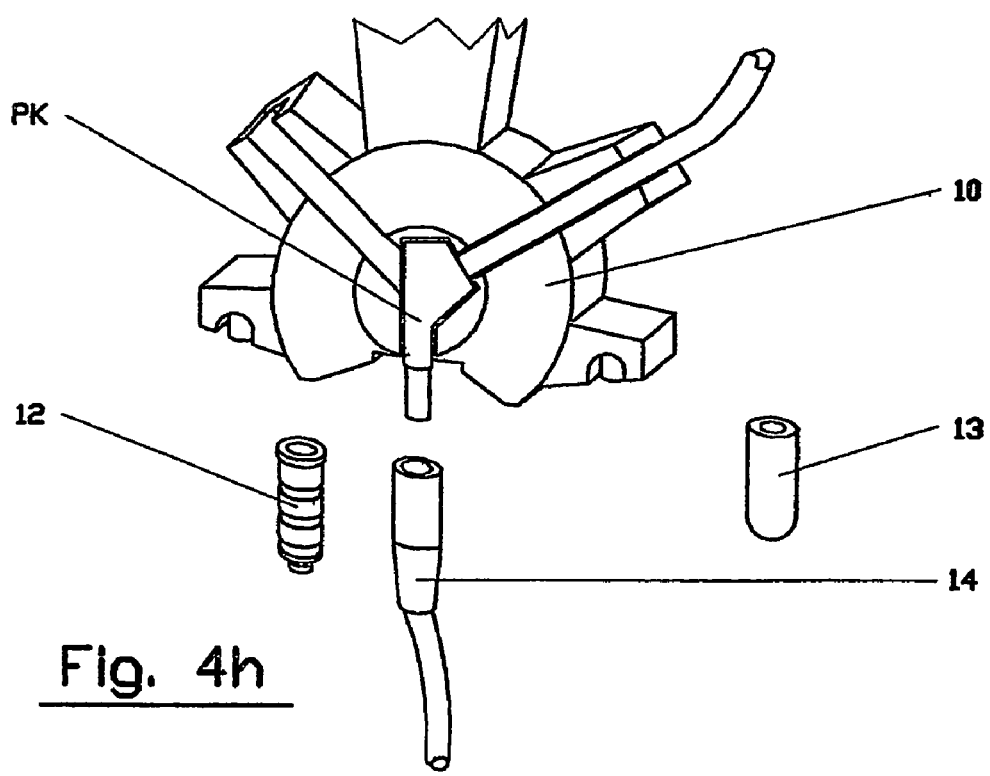
Figure 4I:
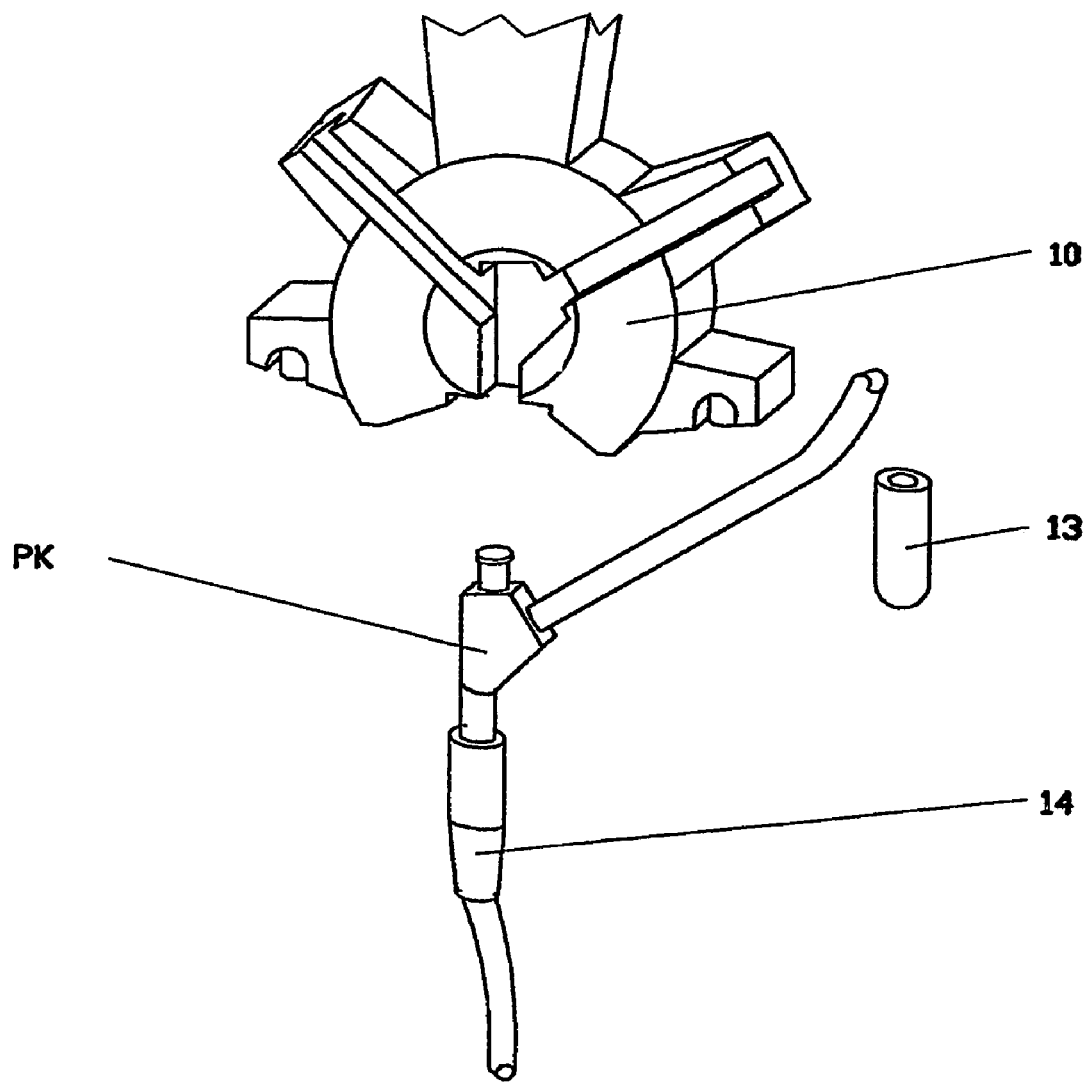

FIG. 4h illustrates how the patient's abdominal connector 14 (without a closure plug 1—this remains in the disinfection cap 11, which, in the disconnected state, sits on the abdominal connector 14) is then reconnected with the patient connector (PK).

The patient connector PK is now (FIG. 4i) again provided with a closure plug 1, and the push-button 4 can be actuated again in order to perform the next disconnection procedure with the closure plug 1.

FIG. 5a to 5e show the assembly and application of a reloading device 12 for reloading a patient connector PK with a. closure plug 1; the device has a movable actuating mechanism 15 for transferring the closure plug 1. In FIGS. 5a to 5c, the actuating mechanism is shown in its starting position. The first step (FIGS. 5b and 5c) comprises screwing the reloading device 12 onto the free end of the patient connector PK. The second step (FIG. 5d and FIG. 5e) comprises moving the actuating device 15, which is illustrated as a manually operated plunger, and thereby pushing the closure plug 1 out of its protected position in the reloading device 12 and into the patient connector PK; as a result, the actuating button 4 of the patient connector PK is returned to the extended position, from where it can be actuated again.

FIG. 6a to FIG. 6c illustrate an alternative version of a reloading device 12 of this kind. Here too, the first step (FIG. 6b) comprises screwing the reloading device onto the free end of the patient connector (PK). In this embodiment, the housing 7, which surrounds and protects the tube section 2 with the closure plug 1, is provided with an internal thread 16. The tube section 2 has a corresponding external thread 17. FIG. 6c illustrates how screwing the rear portion—i.e. the portion that holds the tube section 2—of the reloading device 12 with the housing 7 displaces the closure plug 1 and returns the actuating button 4 to its starting position again.

The invention claimed is:

1. A combination patient connector for peritoneal dialysis and device (12) for loading a new closure plug into the patient connector (PK) whose closure plug has already been used, said patient connector comprising a housing and a movable actuator formed by a push button or turning knob, and said device consisting of a housing (3, 7) containing the new closure plug (1) and of a reloading device (2, 8) for transferring the new closure plug (1) out of the device (12) and into one end of the patient connector (PK), wherein transferring the new closure plug into the patient connector moves the push button or turning knob from a used position to a starting position, and produces a fluid connection with a single linear movement.

2. The device of claim 1, wherein the housing (3, 7) is connectable with the portion of the patient connector (PK) into which the new closure plug (1) is to be transferred.

3. The device of claim 2, wherein the housing (3, 7) can be connected with the patient connector (PK) by means of a positive connection.

4. The device of claim 2, wherein the housing (3, 7) can be connected with the patient connector (PK) by means of a friction-type connection.

5. The device of claim 1, wherein the reloading device is engineered as a push-button or turning knob at the opposite end of the housing (7) to where the new closure plug (1) exits the housing, with an intermediate element being provided between the push-button br turning knob and the new closure plug (1).

6. The device of claim 1, wherein the reloading device is designed as a holder (2) for the new closure plug (1), the retention force exerted by said holder on the new closure plug (1) being lower than the retention force exerted on the new closure plug (1) in the patient connector (PK).

7. The device of claim 1, wherein prior to transfer, the new closure plug (1) is held in a retracted position within the housing (3,7) so as to be protected from contamination.

8. A method for loading a new closure plug into a patient connector (PK) whose closure plug has been used, the patient connector having a movable actuator comprising a push button or turning knob and being adapted to be connected to a tube inserted into a patient's abdominal cavity for peritoneal dialysis, the method comprising the following steps:
   connecting a housing (3, 7) containing the new closure plug (1) with the portion of the patient connector (PK) into which the new closure plug (1) is to be transferred, and
   subsequently transferring the new closure plug (1) out of the housing (3, 7) and into the patient connector (PK), said step of transferring moving the push button or turning knob from a used position to a starting position, and creating a fluid connection by means of a single linear movement, so that the patient connector can be used again.

9. The method of claim 8, wherein the housing (3, 7) is connected with the patient connector (PK) by means of a positive connection or a friction-type connection.

10. The method according to claim 8, wherein the new closure plug (1) is transferred by linear displacement from the housing (3, 7) into the patient connector (PK).

11. The method according to claim 8, wherein the linear displacement of the new closure plug (1) is triggered by actuation of a push-button or turning knob (8).

12. The method according to claim 8, wherein the new closure plug (1) is transferred on account of the retention force exerted by a holder on the new closure plug (1) in the housing (3,7) being lower than a holding force exerted on the new closure plug (1) in the patient connector (PK).

* * * * *